United States Patent [19]

Erickson

[11] Patent Number: 4,751,347

[45] Date of Patent: Jun. 14, 1988

[54] PROCESS FOR TRANSFERRING CYTOPLASMIC ELEMENTS IN BRASSICA, AND PRODUCTS THEREOF

[75] Inventor: Larry Erickson, Mississauga, Canada

[73] Assignee: Allelix, Inc., Mississauga, Canada

[21] Appl. No.: 927,943

[22] Filed: Nov. 7, 1986

[51] Int. Cl.[4] ............................................. A01H 5/02
[52] U.S. Cl. .......................................... 800/1; 47/58; 47/DIG. 1
[58] Field of Search ................... 47/58, DIG. 1; 800/1

[56] References Cited

U.S. PATENT DOCUMENTS 4,517,763  5/1985  Beversdorf et al.

OTHER PUBLICATIONS

W. D. Beversdorf, et al., Can. J. Genet. Cytol. 22: 167–172, 1980.
L. Erickson, et al., Theor. Appl. Genet, 72:151–157, 1986.
L. Erickson, et al., Current Genetics, 9:679–682, 1985.
Z. Fan, et al., Can. J. Plant Sci., 66: 229–234, Apr. 1986.
Phan V. Chuong, et al., Plant Science, 39, pp. 219–226, 1985.
C. S. Levings III, et al., 1976 Proceedings of the Thirty-First Annual Corn and Sorghum Research Conference.
Mary F. Conde, The Journal of Heredity, 70: 2–4, 1979.
Palmer et al, Nature, 301: 725–28, 1983.

*Primary Examiner*—Robert E. Bagwill
*Attorney, Agent, or Firm*—Schwartz, Jeffery, Schwaab, Mack, Blumenthal & Evans

[57] ABSTRACT

Pollen-mediated transferral of cytoplasmic genetic elements can be exploited in a breeding program, for example, to produce cybrids, that employs Brassica plants.

17 Claims, No Drawings

PROCESS FOR TRANSFERRING CYTOPLASMIC ELEMENTS IN BRASSICA, AND PRODUCTS THEREOF

BACKGROUND OF THE INVENTION

An important aspect of many plant improvement programs is the availability of cytoplasmic male sterility (CMS) for use in producing hybrids, as disclosed in U.S. Pat. No. 4,517,763, the contents of which are hereby incorporated by reference. Since CMS in plants is the result of interaction between heritable nuclear and cytoplasmic factors, manipulation of those factors by sexual hybridization has been the strategy of choice when the availability of a male sterile line is deemed essential, for example, in producing F1 hybrid seed on a commercial scale. But sexual manipulation of CMS is limited by the fact that cytoplasmic elements, including the genetic determinants encoding CMS, are typically inherited from the maternal (seed-bearing) plant only, except in a few nonagronomic species.

By the same token, it is generally believed that the contribution of the male (pollen-producing) parent in agronomic species, including those of the genus Brassica, is restricted to nuclear genes. In other words, the solely maternal inheritance of cytoplasm has been viewed as a barrier to the combining of the respective cytoplasmic traits, such as CMS and triazine resistance, of each parent, except by the use of protoplast fusion and regeneration techniques to create somatic hybrids. But these latter techniques are not widely applicable across the range of agronomic species. In addition, they present problems of relative complexity and expense not usually encountered in conventional hybridization programs.

SUMMARY OF THE INVENTION

It is therefore an object of the present invention to provide a method for producing Brassica hybrids that reflect the cytoplasmic contribution of both parental lines, which method does not require the use of special tissue-culturing or regeneration techniques.

It is also an object of the present invention to provide a Brassica cytoplasmic hybrid ("cybrid") plant that expresses a trait encoded by a cytoplasmic determinant derived from the male (pollen-producing) parent.

In accomplishing the foregoing objects, there has been provided, in accordance with one aspect of the present invention, a process for transferring cytoplasmic elements in Brassica, comprising the steps of (a) fertilizing a seed-producing Brassica plant with pollen that contains at least one cytoplasmic element, the presence of which can be detected in progeny of the plant that inherits the element; and (b) selecting among progeny of the plant for the presence of the element. In one preferred embodiment, the cytoplasmic element is a CMS-encoding genetic determinant associated with mitochondria.

In accordance with another aspect of the present invention, a Brassica plant which is the product of the above-described process is also provided. In a preferred embodiment, the seed-producing plant used in the process contains triazine-resistant *Brassica campestris* cytoplasm, and the fertilizing pollen is derived from one or more *Brassica napus* plants that contain polima-type cytoplasm.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

Figure 1:
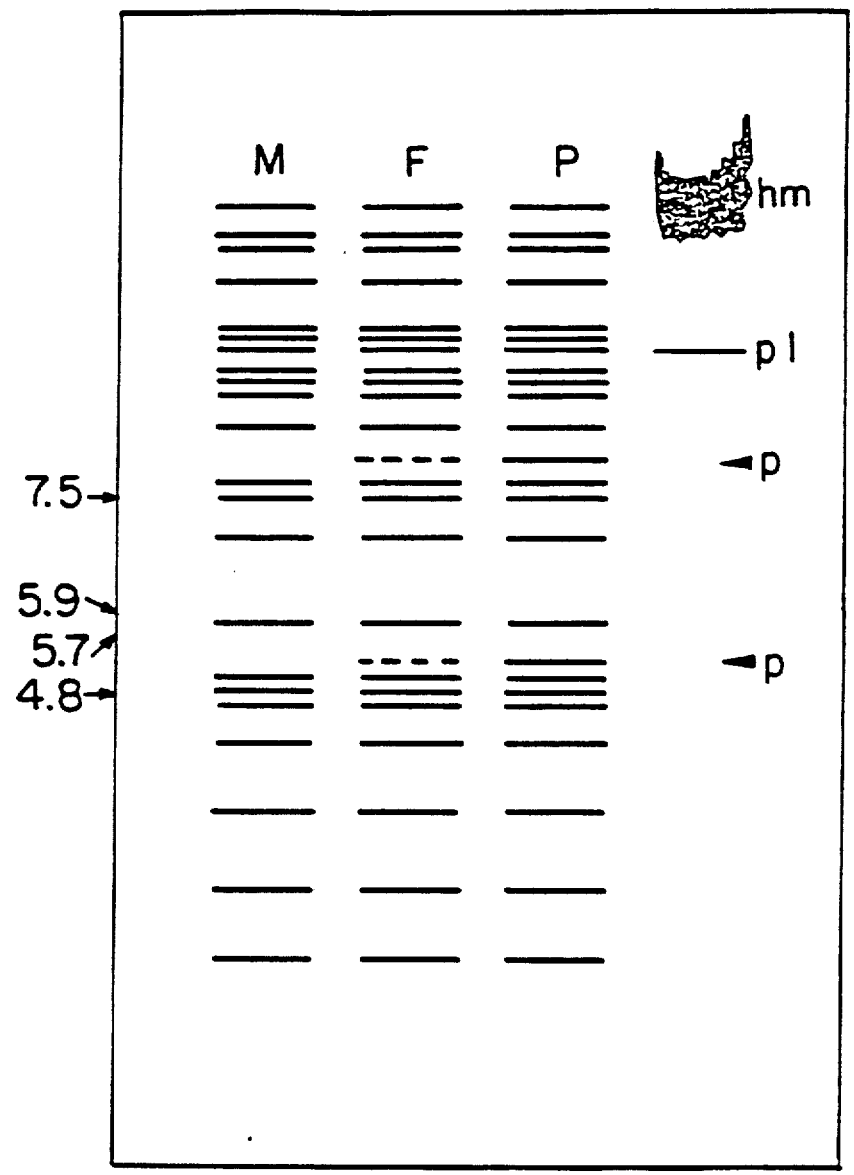
FIG. 1 is a schematic diagram depicting a gel electrophoretic pattern that is distinctive of mitochondrial (mt) DNA extracted from a particular type (polima) of Brassica cytoplasm and digested by the restriction endonuclease PstI. The numbers along the left margin of FIG. 1 represent a nonlinear scale, in kilobase pairs (kb), of fragment sizes.

For purposes of the present description, the terms "cultivar" and "variety" are used synonymously to refer to a group of plants within a species which share certain constant characters that separate them from the typical form and from other putative varieties within that species. While possessing at least one distinctive trait, a variety is also characterized by a substantial amount of overall variation between individuals within the variety, based primarily on the Mendelian segregation of traits among the progeny of succeeding generations. A "line" denotes a group of plants that share a common, defined parentage.

Contrary to conventional wisdom regarding uniparental (maternal) inheritance of nonnuclear genetic factors ("cytoplasmic determinants"), see, e.g., N. W. GILLHAM, ORGANELLE HEREDITY (1978), it has been found that cytoplasmic traits like CMS can be transmitted through pollen in Brassica. More specifically, a natural system for pollen transmission of cytoplasmic determinants has been discovered which can be exploited, in accordance with the present invention, to effect sexually-mediated transfer of CMS from a male parental line, particularly in the course of cytoplasm hybridization ("cybridization"), in Brassica.

The term "Brassica" is used here to denote crop plants in six major species as described, for example, by Yarnell, *Bot. Rev.* 22: 81 (1956). These include three diploid species, *B. nigra* (bb), *B. campestris* (aa) and *B. oleracea* (cc), that are the progenitors of the allotetraploid species *B. juncea* (aabb), *B. napus* (aacc) and *B. carinata* (bbcc). Also included within "Brassica" are the numerous subspecies or varieties that comprise a range of forms resulting from divergent selection during domestication of the aforesaid species.

The following examples illustrate the use of Brassica pollen to transfer cytoplasmic elements—a mitochondria-associated plasmid and a CMS determinant, respectively—from two different male Brassica lines, designated "OAC-SRS-81-02" and "84-5-0012," to another Brassica line characterized by the presence of a distinctive cytoplasm. The latter cytoplasm-type, derived from *B. campestris* as described by Beversdorf et al, "Transfer of Cytoplasmically-Inherited Triazine Resistance from Bird's Rape to Cultivated Oilseed Rape . . .," *Can. J. Genet. Cytol.* 22: 167–72 (1980), includes chloroplasts that impart triazine-resistance, a convenient market trait for following the distribution of maternal "campestris cytoplasm" in the progeny.

It is preferred that the pollen-producing parent employed in the present invention contains cytoplasm of the "polima" (pol) type, which is associated with a distinctive flower morphology and mitochondrial (mt) DNA restriction pattern, as described in greater detail below. It has been discovered that polima cytoplasm carries a genetic determinant for male sterility which can be masked in the male line by the presence, in single or double dosage, of a dominant nuclear restorer gene (Rf).

It is preferred for the maternal line to be recessive for fertility restoration (rf/rf), so that the existence of partial or complete male sterility and polima flower morphology can be employed as criteria for selection of those F1 plants carrying a pattern cytoplasmic contribution, transmitted via the pollen. But the progeny can also be screened for the presence of a distinctive, paternal DNA restriction pattern, like the mt-DNA pattern which is indicative of polima cytoplasm.

The crosses involving the above-mentioned male Brassica lines, as elaborated below, illustrate the manner in which the newly-discovered pollen transmission system is employed, according to the present invention, for cybridization purposes. In particular, the pollen-producing parent must carry a cytoplasmic element that is inherited by progeny receiving paternal cytoplasm and, hence, can serve as a marker, either phenotypic or molecular, "tagging" the cytoplasmic contribution of the male parent through subsequent generations. A mitochondrial element, i.e., an element that is actually part of the mitochondrial genome or that is associated with mitochondria (like a plasmid), is one preferred example of a suitable cytoplasmic marker. In any event, assaying the progeny for presence of the element, or for a phenotypic correlate of the element, can be carried out in the F1 or later generations.

When the marker for the pollen-transmitted cytoplasm is a genetic determinant for male sterility, as is the case in the preferred 84-5-0012 ("012") line, it is also preferable that the male parent carry a determinant that encodes fertility restoration. Alternatively, any method for rendering the pollen-producing parent at least partially male-fertile, as by chemically treating that parent with gibberellin or another plant hormone which affects fertility, can be employed in lieu of using a restorer determinant for the same basic purpose. In any event, the seed-producing plants are preferably emasculated to prevent self-fertilization of the female parental line.

Seed of the '012 line has been deposited with the American Type Culture Collection (Rockville, MD 20852) under accession No. 40277.

The present invention is further described now by reference to the following illustrative examples:

EXAMPLE 1

Using a Molecular (Plasmid) Marker to Track Pollen-Mediated Transmission of Paternal Cytoplasm.

It was discovered that triazine-resistant (tr) cytoplasm derived from *B. campestris*, and transferred to *B. napus* by Beversdorf et al (1980), contains in moderate concentration an 11.3kb, mitochondria-associated (mt) plasmid previously identified by Palmer et al, "An Unusual Mitochondrial DNA Plasmid in the Genus Brassica," *Nature* 301: 725–28 (1983). A *B. napus* line was developed that comprised tr cytoplasm but that had lost the 11.3kb plasmid (p−). See Erickson et al, "Cytoplasmic Male Sterility in Rapeseed [*Brassica napus* L.] 2. The Role of a Mitochondrial Plasmid," *Theoret. & Appl. Genet.* 72: 151–57 (1986). Seed of the p− line has been deposited with the American Type Culture Collection (Rockville, MD 20852) under accession No. 40278.

Three plants of the p− line (designated "tr/p− 1A," "2A" and "3A," respectively) were crossed, as females, to plants of the plasmid-containing *B. napus* line OAC-SRS-81-02 ("OAC"), a precursor of cv. "Triton." The use of the p− and OAC line in this context, however, is illustrative only, since it has been found that other Brassica lines lacking the 11.3k plasmid—and most *B. napus* lines lack the plasmid—can receive that cytoplasmic element via crosses (as female) to a plasmid-containing line. The *B. napus* cv. "Triton," or other normal rapeseed cultivar containing the plasmid, can be employed as a (male) source for the plasmid.

Mitochondrial DNA extracts from each of the twelve F1 progeny were examined for the presence of the 11.3kb plasmid, using electrophoresis and staining with ethidium bromide as described by Erickson et al, "Linear Mitochondrial Plasmid in Brassica Has Terminal Protein," *Curr. Genetics* 9: 679–82 (1985). More specifically, leaves from the F1 progeny were homogenized in four volumes of Buffer A [0.33M sorbitol, 0.05M Tris, 0.003M EDTA, 0.003M mercapto ethanol, 0.1% BSA (pH 8)], and the resulting composition was filtered. The homogenate was centrifuged at 2500×g for two minutes and the supernatant at 16,000×g for twenty minutes. The crude mitochrondrial pellet thus obtained was resuspended in Buffer A to which were added $MgCl_2$ to 0.01M and DNAse I at 15 μg/gram of leaf tissue.

After a one-hour incubation at 4° C., three volumes of Buffer B [0.30M sucrose, 0.05M Tris, 0.05M EDTA (pH 8.0)] were added, and the resuspended mitochondria were then sedimented at 16,000× g for twenty minutes. The mitochondrial pellet was resuspended in a minimal volume of 0.05M Tris/0.02M EDTA (pH 8), lysed by the addition of SDS to 2%, and thereafter digested with proteinase K (200 μg/ml) at 37° C. for one hour. The resulting preparation was then extracted sequentially with phenol and chloroform (2×), and the DNA therein ethanol-precipitated. The precipitated mt-DNA was subsequently subjected to electrophoresis in 1.0% agarose gels, and then to staining with ethidium bromide (0.5 μg/ml). Visualization of the mt-DNA banding pattern under ultraviolet light revealed that the mt-DNA formed a broad, high-molecular-weight band that was readily distinguishable from the smaller band of the plasmid DNA.

To eliminate ambiguities caused occasionally by heavy background fluorescence, the DNA in the gels was electroblotted onto a membrane (Gene Screen Plus ®, manufactured by New England Nuclear) and probed via hybridization with radiolabelled cloned DNA of the 11.3kb plasmid. (Creation of the plasmid clones, and the details of the electroblotting and hybridization procedures, are disclosed by Erickson et al (1986), cited above, the contents of which are hereby incorporated by reference.) In some instances, plasmid DNA was detected with the probe when staining did not reveal a light-band DNA fraction.

The results of the crosses between plasmid-lacking female and plasmid-containing male parents are shown in Table 1:

TABLE 1

| Female Parent | F1 Progeny | Presence of Plasmid (+/−) |
|---|---|---|
| tr/p− 1A | 1 | + |

TABLE 1-continued

| Female Parent | F1 Progeny | Presence of Plasmid (+/−) |
|---|---|---|
|  | 2 | − |
|  | 3 | + |
| tr/p⁻ 2A | 1 | + |
|  | 2 | + |
|  | 3 | − |
|  | 4 | + |
|  | 5 | + |
| tr/p⁻ 3A | 1 | − |
|  | 2 | + |
|  | 3 | + |
|  | 4 | − |

Among the twelve F1 plants, eight contained the plasmid, indicating that a cytoplasmic contribution, comprising at least a mitochondrial component, had been transmitted to the progeny from the male parent via pollen. Subsequent studies involving several generations of selfing or intercrossing tr/p⁻ plants have not produced plants in which the presence of the 11.3kb plasmid can be detected. These results militate against the possibility that the 11.3kb plasmid had arisen spontaneously, or had gone undetected in very low concentration, in the female line.

EXAMPLE 2

Production of Brassica Cybrids by Pollen-Mediated Transferral of a CMS Determinant.

Triazine-resistant (tr/p⁻) plants were crossed, as females, to plants of the '012 line, i.e., to pollen-producing male parents that contained polima cytoplasm and were heterozygous for a fertility-restorer determinant. The F1 progeny of this cross were screened for a contribution of paternal cytoplasm by analyzing restriction-endonuclease (PstI) digests via gel electrophoresis for the presence of a distinctive mt-DNA pattern (see FIG. 1). The methodology used for DNA extraction and electrophoresis was as described in Example 1. Restriction endonuclease digestion with PstI was conducted, in accordance with accepted practice, following the instructions of the enzyme manufacturer (Bethesda Research Labs, Inc., Bethesda, MD). Other enzymes, such as EcoRI, can also be used to generate a restriction pattern in which mtDNA and plasmid DNA can be distinguished.

In FIG. 1, lanes M and P contain maternal and paternal mt-DNA, respectively, while lane F contains the DNA from a typical F1 progeny [tr/p⁻×'012] with heterogeneous mitochondria. (The paternal bands (p) in the progeny DNA are represented with dotted lines to indicate that they are frequently less intense than the other bands.) The right-most lane in FIG. 1 contains an mt-DNA extract that was not digested with any enzyme, resulting in a large (i.e., high molecular weight) band of mitochondrion chromosomal DNA (hm) and an 11.3kb band (p1) representing the intact plasmid DNA.

The F1 progeny were also examined for the incidence of polima flower morphology. Thus, those plants having no anthers, or showing reduced anthers, and an "open" flower configuration characterized by narrow petals and a spreading of petals at the flower base were identified as containing polima cytoplasm from the '012 line. This determination was generally in agreement with the parallel determinations made based on mt-DNA restriction patterns. More specifically, plants displaying polima flower morphology were always found to contain polima mt-DNA, although a few plants with polima mt-DNA did not have polima-type flowers.

Two maternal plants, designated "tr/p⁻1A-2⁻" and "tr/p⁻3A-5⁻," yielded progeny that were found to have both paternal mt-DNA and polima-type flowers. The intensity of the polima-specific bands indicated variable concentrations of paternal mt-DNA, ranging from considerably less than 50% to considerably more.

Thirteen F1 plants from the cross [tr/p⁻1A-2⁻×'012], and four from the cross [tr/p⁻3A-5⁻×'012], were examined (by analysis of restriction-enzyme patterns) for the presence of paternal mt-DNA. In each set of progeny, two plants had mixed mitochondria; among these, one plant from each set had sterile flowers. The plants displaying mt-DNA heterogeneity either were crossed with full-sibs or were open-pollinated, probably by full-sibs nearby. Seed was planted from the two plants that had sterile flowers and, presumably, polima cytoplasm: D-2-4 (progeny designated HM-1-1,2,3 . . . ) and A1-6-2 (progeny designated HM-2-1,2,3 . . . ). The traizine resistance from the original tr/p⁻ mother plant was retained in the progeny, all of which survived a spraying at the seedling stage with atrazine at a concentration approximately equivalent to a field application of 2.0 kg per hectare. (Control resistance plants survived and control susceptibles died when sprayed with the same atrazine concentration in the same growth chamber as the tr/p⁻ plants.)

All but two of the eighteen progeny of HM-1, and all but one of the twelve progeny of HM-2, showed male sterility and the flower morphology of the polima cytoplasm. Moreover, characterization of organelle DNA in these plants revealed the pattern of the triazine-resistant, maternal cytoplasm chloroplasts (cp) and the mt pattern of the paternal (polima) cytoplasm. The HM-1 and HM-2 progeny thus included true cytoplasmic hybrids, Brassica plants that expressed both the triazine resistance encoded by a maternal cp determinant and the pol CMS encoded by a pollen-transferred mt determinant from the paternal cytoplasm. The polima mitochondria, transmitted through the pollen, had apparently not been lost or randomly assorted to only certain cells and tissues during growth of the plants, such that the offspring presented an array of mt types, but rather had become dominant in most offspring examined.

EXAMPLE 3

Expression of CMS by Brassica Cybrids.

Cybrids produced in accordance with Example 2 were crossed to maintainer lines, designated "Regent" and "Westar," respectively, and to restorer lines designated "84-5-0012" and "A0093." The terms "maintainer" and "restorer" are understood by those or ordinary skill to denote lines that are used, respectively, in crosses to produce progeny that maintain the sterility of the maternal parent (in this case, tr/pol-CMS) or that are restored to male (pollen-producing) fertility. See, generally, Fan et al, "Maintainers and Restorers for Three Male-Sterility-Inducing Cytoplasms in Rape (*Brassica napus* L.)," *Can. J. Plant Sci.* 66: 229–34 (1986). In the production of hybrids, the maintainer plants are fertile but otherwise genetically identical counterparts to the CMS plants with which they are grown, typically in alternating strips, to produce seed from the male-sterile line. Conversely, a restorer line, which is homozygous for a genetic determinant encoding fertility restoration of the male-sterile cytoplasm, can be grown with the CMS line so that fertile, pollen-producing progeny result.

Since the maintaining and restoring functions of the above-mentioned lines were known to be specific to pol CMS, it followed that cybrids containing polima cytoplasm derived from a pollen-producing parent should yield progeny of a predetermined character when crossed with either of the maintainer or restoring lines, i.e., CMS should be maintained or fertility restored, respectively. In fact, crosses to the above-mentioned lines did produce progeny that displayed, under greenhouse conditions, the male sterility or fertility expected for maternal plants containing polima cytoplasm.

Moreover, the progeny of backcrosses to the CMS plants produced under the greenhouse conditions were characterized by the stable expression of both male sterility and triazine resistance under field conditions, i.e., when large (on the order of 9 m$^2$ each), substantially uniform stands of cybrids produced according to the present invention were cultivated. By this same basic approach, cybrid lines can be produced. It is preferable that a Brassica line produced in accordance with the present invention should be derived from double haploid parents, i.e., parent plants which are homozygous at all genetic loci. Doubled haploids can be produced in Brassica via microspore-derived embryogenesis, as disclosed, e.g., by Chuong & Beversdorf, *Plant Sci.* 39: 219-26 (1985), the contents of which are hereby incorporated by reference. By the same token, doubled haploids can be produced from F1 plants, or subsequent generations, that are the products of a process within the present invention.

Compared to reported approaches to producing cybrids in rapeseed and other Brassica crops, the present invention permits an unexpectedly high (around 10% or higher) frequency of transfer of paternal characteristics. In addition, the present invention has the advantages of simplicity, speed and very low cost; only conventional growth facilities are required. No special technical expertise or equipment is needed to perform crosses, or to identify cybrid progeny, pursuant to the invention. Many normal, healthy cybrids can be produced, following the present invention, within about six months, and none display the abnormal plant morphology or female sterility often observed in plants regenerated from fused protoplasts.

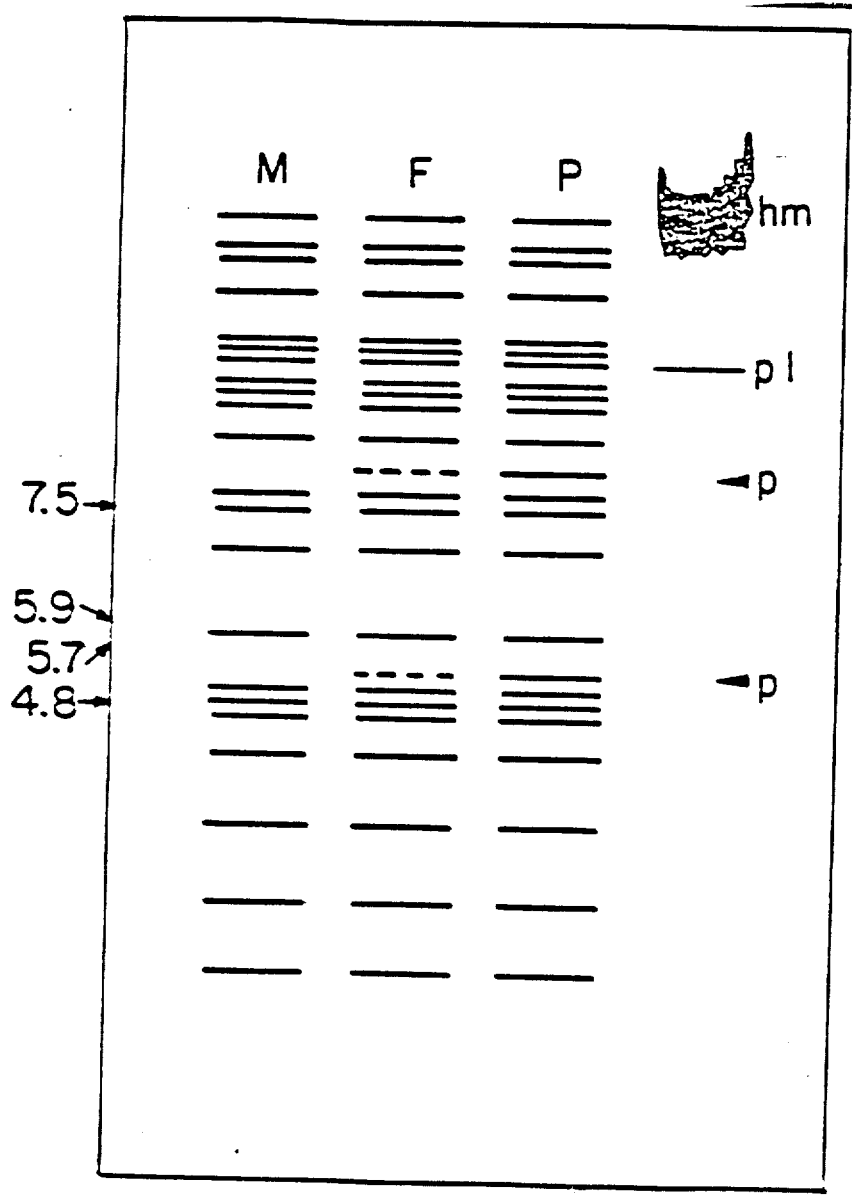

What is claimed is:

1. A process for transferring cytoplasmic elements in Brassica, comprising the steps of:
   (A) fertilizing a seed-producing Brassica plant with pollen that contains at least one cytoplasmic element, the presence of which can be detected in progeny of said plant that inherit said element; and
   (B) selecting among progeny of said plant for the presence of said element.
2. A process according to claim 1, wherein said element is a genetic determinant for male sterility.
3. A process according to claim 2, wherein said determinant is a mitochondrial determinant.
4. A process according to claim 2, wherein said pollen further contains a nuclear genetic determinant that encodes fertility restoration.
5. A process according to claim 1, wherein said element is an 11.3kb mitochondrial plasmid.
6. A process according to claim 1, wherein said seed-producing plant expresses a trait encoded by a cytoplasmic determinant which is inherited by progeny selected in step (B).
7. A process according to claim 6, wherein said trait is triazine-resistance.
8. A Brassica plant which is the product of the process claimed in claim 6.
9. A substantially homogeneous stand of Brassica plants derived from at least one plant as claimed in claim 8.
10. A process according to claim 1, wherein said seed-bearing plant is a rapeseed plant.
11. A process according to claim 10, wherein (i) said pollen is produced by at least one plant containing polima cytoplasm and (ii) said seed-producing plant contains *B. campestris* cytoplasm which imparts triazine resistance.
12. A process according to claim 1, wherein said pollen is produced by at least one plant having the characteristics of *B. napus* 84-5-0012.
13. A process according to claim 1, wherein said seed-bearing plant is incapable of self-fertilization.
14. A process according to claim 1, wherein said progeny comprise the F1 generation of said plant.
15. A Brassica plant which is the product of the process claimed in claim 1.
16. A substantially homogeneous stand of Brassica plants derived from at least one plant as claimed in claim 15.
17. A Brassica line derived from at least one plant produced by the process claimed in claim 1.

* * * * *

UNITED STATES PATENT AND TRADEMARK OFFICE
CERTIFICATE OF CORRECTION

PATENT NO. : 4,751,347

DATED : June 14, 1988

INVENTOR(S) : Larry Erickson

It is certified that error appears in the above-identified patent and that said Letters Patent is hereby corrected as shown below:

The title page showing the illustrative figure should appear as shown on the attached sheet.

The sheet of drawing consisting of Fig. 1, should appear as shown on the attached sheet.

Signed and Sealed this

Sixteenth Day of January, 1990

*Attest:*

JEFFREY M. SAMUELS

*Attesting Officer*      *Acting Commissioner of Patents and Trademarks*

United States Patent [19]

Erickson

[11] Patent Number: 4,751,347
[45] Date of Patent: Jun. 14, 1988

[54] PROCESS FOR TRANSFERRING CYTOPLASMIC ELEMENTS IN BRASSICA, AND PRODUCTS THEREOF

[75] Inventor: Larry Erickson, Mississauga, Canada
[73] Assignee: Allelix, Inc., Mississauga, Canada
[21] Appl. No.: 927,943
[22] Filed: Nov. 7, 1986
[51] Int. Cl.⁴ .................................................. A01H 5/02
[52] U.S. Cl. .................................................. 800/1; 47/58; 47/DIG. 1
[58] Field of Search .................... 47/58, DIG. 1; 800/1
[56] References Cited

U.S. PATENT DOCUMENTS 4,517,763 5/1985 Beversdorf et al.

OTHER PUBLICATIONS

W. D. Beversdorf, et al., Can. J. Genet. Cytol. 22: 167-172, 1980.
L. Erickson, et al., Theor. Appl. Genet. 72:151-157, 1986.
L. Erickson, et al., Current Genetics, 9:679-682, 1985.
Z. Fan, et al., Can. J. Plant Sci., 66: 229-234, Apr. 1986.
Phan V. Chuong, et al., Plant Science, 39, pp. 219-226, 1985.
C. S. Levings III, et al., 1976 Proceedings of the Thirty-First Annual Corn and Sorghum Research Conference.
Mary F. Conde, The Journal of Heredity, 70: 2-4, 1979.
Palmer et al, Nature, 301: 725-28, 1983.

Primary Examiner—Robert E. Bagwill
Attorney, Agent, or Firm—Schwartz, Jeffery, Schwaab, Mack, Blumenthal & Evans

[57] ABSTRACT

Pollen-mediated transferral of cytoplasmic genetic elements can be exploited in a breeding program, for example, to produce cybrids, that employs Brassica plants.

17 Claims, 1 Drawing Sheet